(12) United States Patent
Beaulieu et al.

(10) Patent No.: US 9,522,206 B2
(45) Date of Patent: Dec. 20, 2016

(54) METHODS FOR TREATING ODORS

(71) Applicant: EXP SERVICES INC., Brampton (CA)

(72) Inventors: Martin Beaulieu, Sainte-Foy (CA); Stéphane Chabot, Lévis (CA); Yves Charest, Ancienne-Lorette (CA)

(73) Assignee: EXP SERVICES INC., Brampton (CA)

( * ) Notice: Subject to any disclaimer, the term of this patent is extended or adjusted under 35 U.S.C. 154(b) by 0 days.

(21) Appl. No.: 14/836,757

(22) Filed: Aug. 26, 2015

(65) Prior Publication Data

US 2015/0359917 A1   Dec. 17, 2015

Related U.S. Application Data

(62) Division of application No. 12/989,155, filed as application No. PCT/CA2009/000641 on May 8, 2009, now abandoned.

(Continued)

(51) Int. Cl.
*B01J 8/00* (2006.01)
*A62D 3/00* (2006.01)
(Continued)

(52) U.S. Cl.
CPC .. *A61L 9/00* (2013.01); *A61L 9/16* (2013.01); *A61L 9/20* (2013.01); *B01D 53/44* (2013.01); *C02F 1/722* (2013.01); *C02F 1/725* (2013.01); *B01D 2251/106* (2013.01); *B01D 2251/304* (2013.01); *B01D 2251/604* (2013.01); *B01D 2251/70* (2013.01); *B01D 2251/902* (2013.01); *B01D 2257/90* (2013.01); *C02F 1/283* (2013.01); *C02F 1/32* (2013.01); *C02F 1/683* (2013.01); *C02F 2303/02* (2013.01); *C02F 2303/18* (2013.01)

(58) Field of Classification Search
CPC ............... A61L 9/00; A61L 9/01; C02F 1/00; B05B 17/00; A01N 63/00
USPC .............. 422/4–5, 28; 423/245.2; 252/186.1, 252/182.11; 261/78.1, 115
See application file for complete search history.

(56) References Cited

U.S. PATENT DOCUMENTS 4,012,321 A   3/1977   Koubek
4,443,342 A   4/1984   Stas et al.
(Continued)

FOREIGN PATENT DOCUMENTS

CA   2178258   12/1996
CA   2527450   1/2006
(Continued)

OTHER PUBLICATIONS

Walling, "Fenton's Reagent Revisited", Accounts of Chemical Research vol. 8, 1974. pp. 125-131.
(Continued)

*Primary Examiner* — Monzer R Chorbaji
(74) *Attorney, Agent, or Firm* — Bereskin & Parr LLP/S.E.N.C.R.L., s.r.l.

(57) ABSTRACT

There are provided methods for treating a fluid having an undesirable odor. The methods comprise contacting the fluid with a $H_2O_2$ basic aqueous oxidizing composition and/or with a $H_2O_2$ acidic aqueous oxidizing composition. Optionally, the fluid can be further treated by contacting it with activated carbon and/or by submitting the fluid and the composition to UV radiation when they are contacting together.

19 Claims, 3 Drawing Sheets

Related U.S. Application Data

(60) Provisional application No. 61/051,716, filed on May 9, 2008.

(51) Int. Cl.
  *A61L 9/00* (2006.01)
  *A61L 9/16* (2006.01)
  *A61L 9/20* (2006.01)
  *B01D 53/44* (2006.01)
  *C02F 1/72* (2006.01)
  *C02F 1/28* (2006.01)
  *C02F 1/32* (2006.01)
  *C02F 1/68* (2006.01)

(56) References Cited

U.S. PATENT DOCUMENTS

| | | | |
|---|---|---|---|
| 4,446,029 | A | 5/1984 | Betermier et al. |
| 4,780,287 | A | 10/1988 | Zeff et al. |
| 5,043,080 | A | 8/1991 | Cater et al. |
| 5,266,214 | A | 11/1993 | Safarzedeh-Amiri |
| 5,348,665 | A | 9/1994 | Schulte et al. |
| 5,480,524 | A | 1/1996 | Oeste |
| 5,762,808 | A | 6/1998 | Peyton |
| 5,914,305 | A | 6/1999 | Madison et al. |
| 5,919,982 | A | 7/1999 | Whittaker et al. |
| 6,315,963 | B1 | 11/2001 | Speer |
| 6,503,471 | B1 | 1/2003 | Han et al. |
| 6,521,809 | B1 | 2/2003 | Smith et al. |
| 7,163,665 | B2 | 1/2007 | Kato |
| 7,550,123 | B2 | 6/2009 | Temple et al. |
| 2001/0043898 | A1 | 11/2001 | Stoltz et al. |
| 2002/0189929 | A1* | 12/2002 | Kato .................. B01D 53/007 204/157.15 |
| 2005/0178733 | A1 | 8/2005 | Conger et al. |
| 2005/0274623 | A1 | 12/2005 | Soler Turu et al. |
| 2007/0059229 | A1* | 3/2007 | Temple .................. A61L 9/145 423/243.01 |
| 2007/0081933 | A1 | 4/2007 | Chabot et al. |
| 2010/0258428 | A1 | 10/2010 | Gignac et al. |
| 2011/0189049 | A1 | 8/2011 | Beaulieu et al. |

FOREIGN PATENT DOCUMENTS

| | | |
|---|---|---|
| CA | 2721684 | 11/2009 |
| EP | 1206906 | 5/2002 |
| WO | 9936160 | 7/1999 |
| WO | 0015734 | 3/2000 |
| WO | 0207860 | 1/2002 |
| WO | 2004030797 | 4/2004 |
| WO | 2007041831 | 4/2007 |
| WO | 2010118530 | 10/2010 |

OTHER PUBLICATIONS

English Abstract of JP55056820, published on Apr. 26, 1980.
English Abstract of DE 197 53 117, published on Jun. 18, 1998.
Ferrero, "Oxidative degradation of dyes and surfactant in the Fenton and photo-Fenton treatment of dyehouse effluents", Journal of the Society of Dyes and Colourists, vol. 113, May/Jun. 2000, pp. 148-153.
Tudorache et al., "Advanced purification of wastewater of the cellulose and paper industry by Fenton-type oxidation processes", Studii si Cercetari Scientificie: Chimie si Enginerie Chimica, Biotechnologi, Industrie alimentara, vol. 7, Issue 2, pp. 337-348 (2006) (Translation).
Tudorache et al., "Advanced purification of wastewater of the cellulose and paper industry by Fenton-type oxidation processes", Studii si Cercetari Scientificie: Chimie si Enginerie Chimica, Biotechnologi, Industrie alimentara, vol. 7, Issue 2, pp. 337-348 (2006).
English Abstract of CN1524604, published on Sep. 1, 2004.
English Abstract of DE3221795, published on Dec. 15, 1983.
English Abstract of JP5228333, published on Sep. 7, 1993.
English Abstract of JP6142440, published on May 24, 1994.
English Abstract of JP52000217, published on Jan. 5, 1977.
English Abstract of JP62171798, published on Jul. 28, 1987.
Zepp, "Hydroxyl Radical Formation in Aqueous Reactions (pH 3-8) of Iron(II) with Hydrogen Peroxide: The Photo-Fenton Reaction", Environ. Sci. Technol. 1992, 26, 313-319.
Kwan et al., "Transformation of 2,4-dichlorophenoxy-ethanoic acid (2,4-D) by a photoassisted ferrous oxalate/H2O2 system", J. Chem Technol Biotechnol 79:663-669 (online: 2004).
Kajitvichyanukul et al., "Formaldehyde degradation in the presence of methanol by photo-Fenton process", Journal of Environmental Management 86 (2008) 545-553.
Pignatello et al., "Advanced Oxidation Processes for Organic Contaminant Destruction Based on the Fenton Reaction and Related Chemistry", Critical Reviews in Environmental Science and Technology, 36:1-84, 2006.
McGinnis et al., "Degradation of Ethylene Glycol in Photo Fenton Systems", Wat. Res. vol. 34, No. 8, pp. 2346-2354, 2000.
English Abstract of DE19607389, "Absorption of nitrogen oxides from effluent gases by contact with aqueous solution containing hydrogen peroxide, nitric acid and peroxide activator", published on Sep. 4, 1997.
Arana et al., "Highly concentrated phenolic wastewater treatment by the Photo-Fenton reaction, mechanism study by FTIR-ATR", Chemosphere vol. 44 (2001) pp. 1017-1023.
Litter, "Heterogenous photocatalysis: Transition metal ions in photocatalytic systems", Applied Catalysis B: Environmental 23 (1999) pp. 89-114.

* cited by examiner

METHODS FOR TREATING ODORS

CROSS-REFERENCE TO RELATED APPLICATIONS

This application is divisional application of U.S. Ser. No. 12/989,155 filed on Dec. 20, 2010 and that is a 35 USC 371 national stage entry of PCT/CA2009/000641 filed on May 8, 2009 and which claims priority from U.S. provisional application No. 61/051,716 filed on May 9, 2008. These documents are hereby incorporated by reference in their entirety.

TECHNICAL FIELD

The present document relates to the field of odor treatment. More particularly it relates to methods for treating odors. For example, odors present in a fluid can be treated by using such methods.

BACKGROUND OF THE DISCLOSURE

Industrial activity has always generated odors in the ambient air which were and are still able to worry the neighborhood. Despite the implementation of tighter environmental regulations, this problem remains present even more so since, in certain locations, new commercial and residential sectors are developed in proximity to these sources.

The use of biofilters for reducing the odors has demonstrated its effectiveness. However, their installation requires large surface areas that are not always found on the industrial sites. The odorous gas emitters must then make do with technologies that are more compact and which have limitations due to the nature of the chemical compounds.

Each of the chemical compounds has different characteristics with regard to its solubility in water or another solvent, its olfactory threshold and its partial pressure which ensure that the technologies currently used are limited whether this is as regards the effectiveness of the treatment or else the lifetime of the materials used.

For such situations where a problem of space and of the use of compact technologies reaches limits, it would be highly desirable to be provided with an alternative technology.

SUMMARY OF THE DISCLOSURE

According to one aspect, there is provided a method for method for treating a fluid having an undesirable odor, the method comprising:
 contacting the fluid with a basic aqueous oxidizing composition comprising at least one cation of a metal chosen from Fe, Cu, Ni, Mn, Ti, Cr, Ce, Zn, Pd, Mo, and mixtures thereof and $H_2O_2$; and
 contacting the fluid with an acidic aqueous oxidizing composition comprising at least one cation of a metal chosen from Fe, Cu, Ni, Mn, Ti, Cr, Ce, Zn, Pd, Mo, and mixtures thereof and $H_2O_2$, The fluid can be contacted with the basic aqueous oxidizing composition, and then the fluid can be contacted with the acidic aqueous oxidizing composition, or the fluid can be contacted with the acidic aqueous oxidizing composition, and then the fluid can be contacted with the basic aqueous oxidizing composition. The method can optionally further comprise contacting the fluid with activated carbon.

According to another aspect, there is provided a method for treating a fluid having an undesirable odor, the method comprising:
 contacting the fluid with a basic aqueous oxidizing composition comprising at least one cation of a metal chosen from Fe, Cu, Ni, Mn, Ti, Cr, Ce, Zn, Pd, Mo, and mixtures thereof and $H_2O_2$; and/or contacting the fluid with an acidic aqueous oxidizing composition comprising at least one cation of a metal chosen from Fe, Cu, Ni, Mn, Ti, Cr, Ce, Zn, Pd, Mo, and mixtures thereof and $H_2O_2$; and
 contacting the fluid with activated carbon.

The fluid can be contacted with the basic aqueous oxidizing composition, and then the fluid can be contacted with the acidic aqueous oxidizing composition, or the fluid can be contacted with the acidic aqueous oxidizing composition, and then the fluid can be contacted with the basic aqueous oxidizing composition.

According to another aspect, there is provided a method for treating a fluid having an undesirable odor, the method comprising:
 contacting the fluid with an acidic aqueous oxidizing composition comprising at least one cation of a metal chosen from Fe, Cu, Ni, Mn, Ti, Cr, Ce, Zn, Pd, Mo, and mixtures thereof and $H_2O_2$
 submitting the fluid and the composition to an UV radiation.

The fluid can optionally be further contacted with a basic aqueous oxidizing composition and/or with activated carbon.

It was found that such methods are very effective for treating undesirable and/or unpleasant odors. Such technologies can be operated at low costs and represent a simple manner to treat fluids.

In the methods previously described, the fluid can comprise at least one organic compound chosen from carboxylic acids, thiols, thioethers, disulfides, alcohols, aldehydes, amines, amides and mixtures thereof. The carboxylic acids can comprise $C_1$-$C_{20}$ carboxylic acids. The thiols can comprise $C_1$-$C_{20}$ thiols. The thioethers can comprise $C_2$-$C_{20}$ thioethers. The disulfides can comprise $C_2$-$C_{20}$ disulfides. The alcohols can comprise $C_1$-$C_{20}$ alcohols. The aldehydes can comprise $C_1$-$C_{20}$ aldehydes. The amines can comprise $C_1$-$C_{20}$ amines. The amides can comprise $C_1$-$C_{20}$ amides.

In the methods previously described, the fluid can be passed through a bed of activated carbon. Such a treatment can be carried out before or after a treatment with a basic or acidic oxidizing composition.

The fluid can be treated with the basic aqueous oxidizing composition and then with the acidic aqueous oxidizing composition. Alternatively, the fluid can be treated with the acidic aqueous oxidizing composition and then with the basic aqueous oxidizing composition.

The fluid can be treated with the basic aqueous oxidizing composition so as to at least partially oxidize at least one compound responsible for the undesirable odor and then the fluid can be treated with the acidic aqueous oxidizing composition so as to at least partially oxidize at least one compound responsible for the undesirable odor, thereby at least partially reducing intensity of the undesirable odor.

The fluid can be treated with the acidic aqueous oxidizing composition so as to at least partially oxidize at least one compound responsible for the undesirable odor and then the fluid is treated with the basic aqueous oxidizing composition so as to at least partially oxidize at least one compound responsible for the undesirable odor, thereby at least partially reducing intensity of the undesirable odor.

The methods can further comprise submitting the fluid and the acidic aqueous oxidizing composition to UV radiation, when the fluid and the acidic aqueous oxidizing composition are contacting each other. The method can also further comprise submitting the fluid and the basic aqueous oxidizing composition to UV radiation, when the fluid and the basic aqueous oxidizing composition are contacting each other.

For example, the fluid can be contacted with the acidic aqueous oxidizing composition so as to at least partially dissolve at least one compound responsible for the undesirable odor and contained in the fluid into the acidic aqueous oxidizing composition and wherein the method can further comprise submitting, the at least one compound that is at least partially dissolved into the acidic aqueous oxidizing composition, to UV radiation.

For example, the fluid can be contacted with the basic aqueous oxidizing composition so as to at least partially dissolve at least one compound responsible for the undesirable odor and contained in the fluid into the basic aqueous oxidizing composition and wherein the method can further comprise submitting, the at least one compound that is at least partially dissolved into the basic aqueous oxidizing composition, to UV radiation.

The fluid can be contacted with the acidic aqueous oxidizing composition so as to at least partially dissolve at least one compound responsible for the undesirable odor and contained in the fluid into the acidic aqueous oxidizing composition and the at least one compound that is at least partially dissolved into the acidic aqueous oxidizing composition can be submitted to UV radiation so as to at least partially oxidize the at least one compound and at least partially reduce intensity of the undesirable odor.

The fluid can be treated with the basic aqueous oxidizing composition and/or with the acidic aqueous oxidizing composition so as to at least partially oxidize at least one compound responsible for the undesirable odor and then the fluid can be passed through a bed of activated carbon, thereby at least partially reducing intensity of the undesirable odor.

In the methods previously described, the basic and/or acidic composition can comprise a cation of a metal chosen from Fe, Cu, Ni, Mn, Ti, Cr, Ce, Zn, Pd, Mo, and mixtures thereof. For example, the metal can be Fe, or Cu. In another example, the composition can comprise a cation of Fe.

For example, the cations can be chosen from $Fe^{2+}$, $Cu^{2+}$, $Ni^{2+}$, $Mn^{2+}$, $Ti^{4+}$, $Cr^{3+}$, $Ce^{3+}$, $Zn^{2+}$, $Pd^{2+}$, $Mo^{6+}$, and mixtures thereof. According to another example, the cation can be $Fe^{2+}$, or $Cu^{2+}$. According to another example, the cation can be $Fe^{2+}$.

The sequestering agent (or chelator), when oxidation occurs in a basic aqueous composition, can be chosen from diethylenetriaminepentaacetic acid (DTPA), nitrolotriacetic acid (NTA), ethylenediaminetetraacetic acid (EDTA), sodium hexametaphosphate, sodium citrate, and mixtures thereof. For example, the sequestering agent can be DTPA or NTA. Alternatively, the sequestering agent can be an ion exchange resin such as zeolites. For example, the sequestering agent can be NTA and the cation can be $Fe^{2+}$. The sequestering agent (or chelator), when oxidation occurs in an acidic aqueous composition, can be chosen from ethylenediaminetetraacetic acid (EDTA), oxalic acid, citric acid, glycine, NTA, salicylic acid, sulfosalicylic acid, trithylenetramine, and mixtures thereof. For example, the sequestering agent can be oxalic acid.

For example, the sequestering agent can be present at a concentration of at least 30 mg/L, about 30 mg/L to about 480 mg/L or about 60 mg/L to about 240 mg/L In the previously described methods, contacting can include mixing the fluid with the basic oxidizing composition so as to at least partially dissolve at least one compound contained in the fluid into the basic oxidizing composition. The fluid and the basic oxidizing composition can be mixed together in a packed column. For example, the fluid can be introduced at a bottom portion of the column and the basic aqueous composition can be introduced at a top portion of the column. The fluid and the basic aqueous composition can be mixed together into the column over a predetermined amount of transfer units.

For example, the fluid, before contacting the basic aqueous oxidizing composition, can be at a temperature of about 10° C. to about 85° C., about 25° C. to about 55° C., or about 15° C. to about 40° C.

For example, the metal cation can be present in the basic composition at a concentration of at least 1 mg/mL, at least 5 mg/mL, or at least 20 mg/mL. about 1 mg/L to about 20 mg/L or about 2 mg/L to about 10 mg/L.

For example, the concentration of $H_2O_2$ in the basic composition can be at least 20 mg/L, about 20 mg/L to about 2000 mg/L, or about 50 mg/L to about 700 mg/L.

The basic aqueous oxidizing composition can comprise a base chosen from NaOH, KOH, $Mg(OH)_2$, $Ca(OH)_2$, $NaHCO_3$, $Na_2CO_3$, $K_2CO_3$, $KHCO_3$, and mixtures thereof. The basic composition can have a pH of at least 9.0. For example, the pH can be of about 9.3 to about 11.5, about 9.5 to about 10.5, about 9.7 to about 10.0, or about 9.8.

In the previously described methods, contacting can include mixing the fluid with the acidic oxidizing composition so as to at least partially dissolve at least one compound contained in the fluid into the acidic oxidizing composition. The fluid and the acidic oxidizing composition can be mixed together in a packed column. For example, the fluid can be introduced at a bottom portion of the column and the acidic aqueous composition can be introduced at a top portion of the column. The fluid and the acidic aqueous composition can be mixed together into the column over a predetermined amount of transfer units.

The acidic aqueous oxidizing composition can comprise an acid chosen from $H_2SO_4$, HCl, $HNO_3$, $H_3PO_4$, and mixtures thereof.

The acidic aqueous oxidizing composition can have a pH of at least 1.5, about 1.5 to about 4.0, about 2.0 to about 3.0, or about 2.2 to about 2.6.

The metal cation can be present in the acidic aqueous oxidizing composition at a concentration of at least 5 mg/L, at least 10 mg/L, or at least 20 mg/L. The concentration can also be about 10 mg/L to about 200 mg/L, about 20 mg/L to about 100 mg/L, about 50 to 150 mg/L, or about 30 mg/L to about 50 mg/L. For example such a cation can be $Fe^{2+}$, $Cu^{2+}$ or a mixture thereof. For example, the concentration of $H_2O_2$ in the acidic composition can be at least 100 mg/L, about 100 mg/L to about 3500 mg/L, or about 1000 mg/L to about 2500 mg/L.

For example, $H_2O_2$ can be present in the acidic aqueous oxidizing composition at a molar ratio $H_2O_2$:metal of at least 5:1, at least 10:1, or at least 20:1.

For example, $H_2O_2$ can be present in the acidic aqueous oxidizing composition at a molar ratio $H_2O_2$:metal of about 10:1 to about 100:1, or 12:1 to 40:1.

For example, the fluid, before contacting the acidic aqueous oxidizing composition, can be at a temperature of about 10° C. to about 85° C. or about 15° C. to about 40° C.

In the methods previously defined, the treatment can permit to reduce by at least 50%, by at least 60%, by at least 70%, by at least 75%, by at least 80%, by at least 85%, by at least 90%, by at least 95%, by at least 97%, by at least 98%, of about 50% to about 99%, of about 60% to about 99%, of about 70% to about 97%, or of about 70% to about 99% the intensity of the at least one indesirable odor.

The expression "sequestering agent" as used herein includes chemical moieties that bind to, or complex with, any cation or anion. Examples of sequestering agents or chelators are well known in the art. For example, the sequestering agent can bind to a metal cation.

The expression "packed column" as used herein refers to an absorption tower, in which the packing is used so as to increase contact between a gas and a liquid. For example, such a packed column can be used for removing a contaminant from a gas stream by absorbing it or dissolving it into a liquid (such as an oxidizing composition).

The term "fluid" as used herein refers to a gas, a liquid or a mixture thereof.

BRIEF DESCRIPTION OF DRAWINGS

The following drawings represent in a non-limitative manner, various examples.

DETAILED DESCRIPTION

Further features and advantages will become more readily apparent from the following non-limitative examples:

The following examples are non-limiting examples.

EXAMPLES

In order to determine the effectiveness of each of the treatments that are part of the examples, dynamic olfactometry measurements have been carried out. The olfactometer is composed of six beakers in which three test specimens are found. Each beaker corresponds to a different dilution level of the odorous gas. In each of these beakers, a single test specimen diffuses odorous air. Each of the individuals that make up the panel must identify, in each beaker, which of the test specimens diffuses the odorous gas. If the individual does not detect any odors, the person passes to the next beaker. The data from the panel are compiled and the results are calculated with the aid of a table by using the air dilution and odorous gas flow rates of each of the test specimens.

Example 1

Treatment by Oxidation and Absorption in Consecutive Basic and Acidic Media

Figure 1:
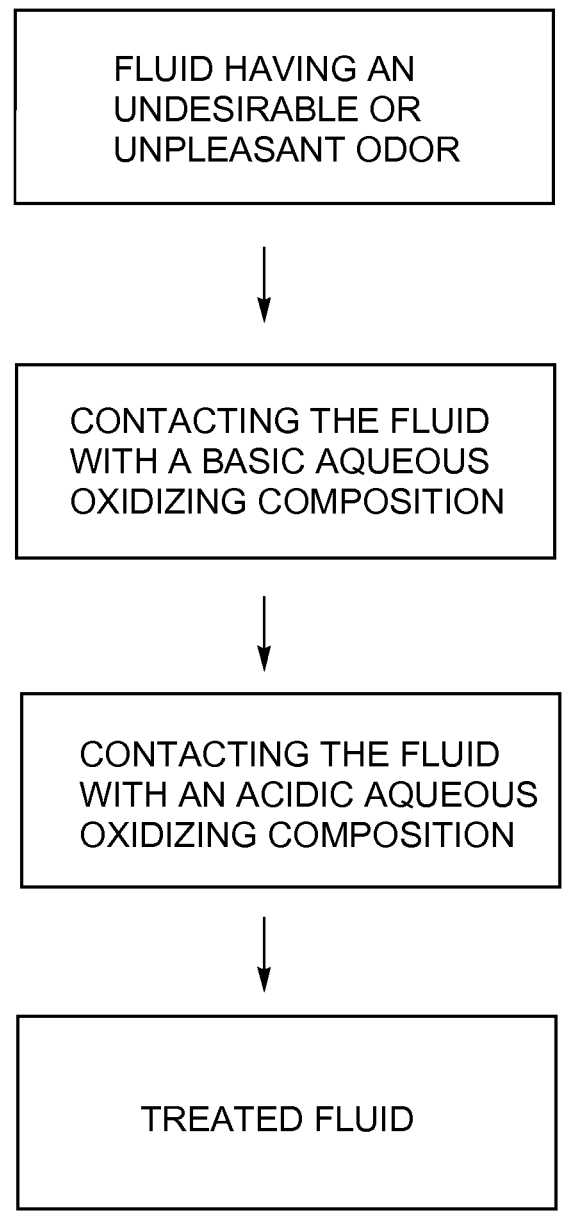
FIG. 1 shows a bloc diagram of an example of a method for treating a fluid.

The gas to be treated contains several organic compounds which, depending on their nature, are more soluble in a basic medium or in an acidic medium. In the present examples, compounds such as butyric acid, valeric acid, sulfides and disulfides were found to be compounds that are more soluble in a basic media and certain amines were found to be more soluble in an acidic media. FIG. 1 is a bloc diagram concerning the method carried out in Example 1.

The gas was treated by passing it through a packed column in which a basic aqueous oxidizing composition (comprising $H_2O_2$ and NaOH and having a pH of about 10.0) was flowing. The oxidizing composition contained about 510 mg/L of hydrogen peroxide, about 4 mg/L of Fe and NTA at a concentration of four times higher than the concentration of Fe on a molar basis. The temperature of the medium was about 22° C. The gas flow rate was about 3000 $m^3/h$. Fe can be provided in various form such as $FeSO_4$, $FeCl_2$ or any suitable source of $Fe^{2+}$. A reactor was disposed at the bottom of the column, and the oxidizing composition was recirculated from the reactor to a top portion of the column by means of a pump. The fluid was introduced at a bottom portion of the column in a counter-current manner.

Then, the gas is treated in a second packed column that also comprises an oxidizing composition comprising hydrogen peroxide. The composition flowing in the second column was an acidic aqueous oxidizing composition ($H_2SO_4$) having a pH of about 2.2. The oxidizing composition contained about 2360 mg/L of hydrogen peroxide, and about 50 mg/L of Fe. The temperature of the medium was about 23° C. The gas flow rate was about 3.6 $m^3/h$.

These conditions were maintained for 19 days and five dynamic olfactometry analyses were carried out. The results were the following (average values):

odor level at the inlet: 131;

odor level after 1st treatment: 69;

effectiveness after 1st treatment: 47%;

odor level after 2nd treatment: 36; and effectiveness after 2nd treatment: 73%.

Example 2

Figure 2:
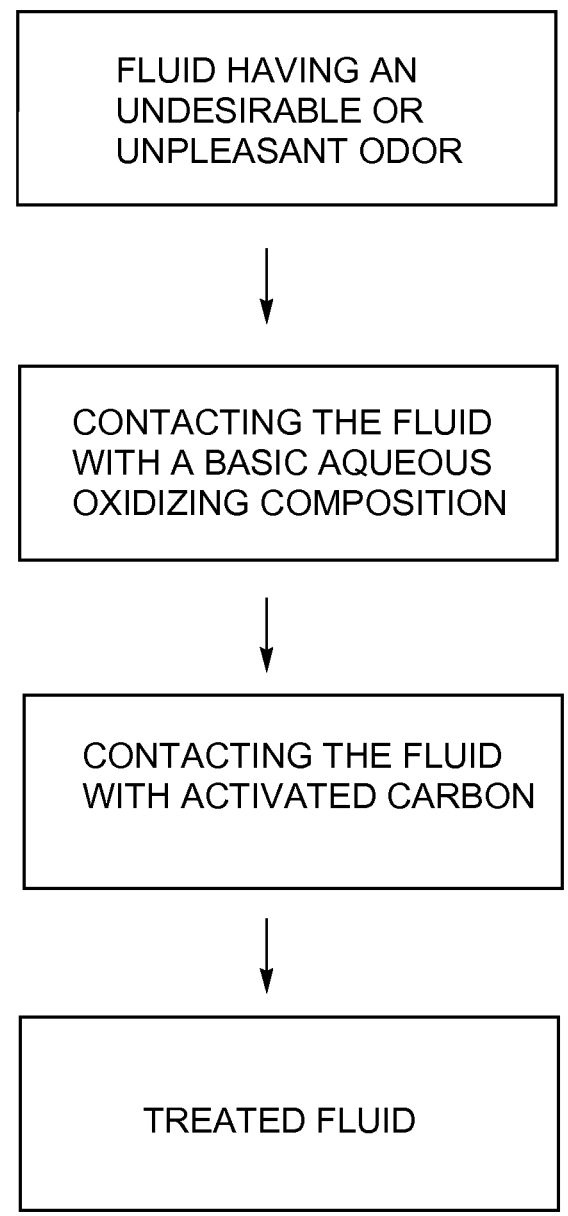
FIG. 2 shows a bloc diagram of another example of a method for treating a fluid.

Treatment by Oxidation and Absorption in a Basic Medium and Adsorption onto Activated Carbon In the present example, a gas similar to the one treated in example 1 was treated by using a similar set-up. FIG. 2 is a bloc diagram concerning the method carried out in Example 2.

The gas was treated by passing it through a packed column in which a basic aqueous oxidizing composition (comprising $H_2O_2$ and NaOH and having a pH of about 9.8) was flowing. The oxidizing composition contained about 75 mg/L of hydrogen peroxide, about 2 mg/L of Fe and NTA at a concentration of four times higher than the concentration of Fe on a molar basis. The temperature of the medium was about 21° C. The gas flow rate was about 2040 $m^3/h$.

Subsequently, the gas was treated by passing it through a bed of activated carbon. The temperature of the gas was about 24° C. at a gas flow rate of about 3 $m^3/h$. The height of the activated carbon was about 180 mm.

These operating conditions were maintained for 5 days and 8 olfactometry measurements were taken. The results are the following:

odor level at the inlet: 155;

odor level after 1st treatment: 70;

effectiveness after 1st treatment: 55%;

odor level after 2nd treatment: 5; and effectiveness after 2nd treatment: 97%.

Example 3

Figure 3:
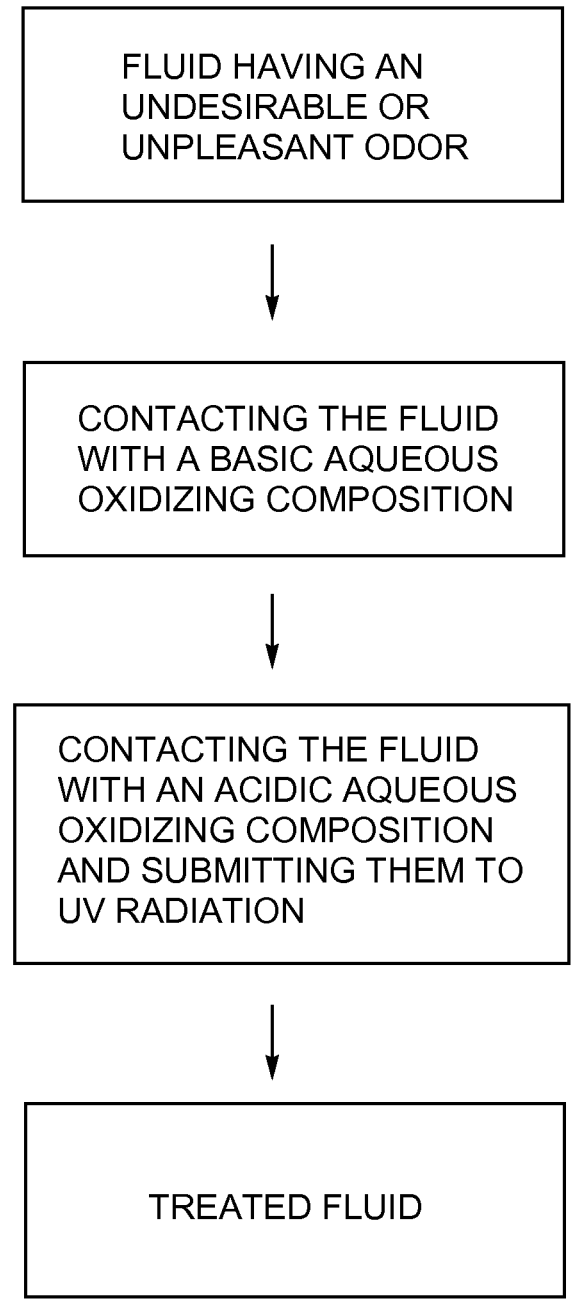
FIG. 3 shows a bloc diagram of a further example of a method for treating a fluid.

Treatment by Oxidation and Absorption in a Basic Media and then, in an Acidic Media in which Oxidation is Enhanced by UV Radiation In the present example, a gas similar to the one in example 1 was treated by using a similar set-up. FIG. 3 is a bloc diagram concerning the method carried out in example 3.

The gas was treated by passing it through a packed column in which a basic aqueous oxidizing composition (comprising $H_2O_2$ and NaOH and having a pH of about 9.8) was flowing. The oxidizing composition contained about 300 mg/L of hydrogen peroxide, about 2 mg/L of Fe and NTA at a concentration of four times higher than the concentration of Fe on a molar basis. The temperature of the medium was about 22° C. The gas was at a temperature of about 50° C. and a flow of 80 L/min.

Then, the gas was treated in a second packed column that also contained an oxidizing composition comprising hydrogen peroxide. The composition flowing in the second column was an acidic aqueous oxidizing composition ($HNO_3$) having a pH of about 2.4. The oxidizing composition contained about 350 mg/L of hydrogen peroxide, about 30 mg/L of Fe and oxalic acid at was concentration of four times higher than the concentration of Fe on a molar basis. The temperature of the medium was about 22° C. The gas flow was about 80 L/min.

As explained in example 1, the mixture of the gas and the composition was flowing down from the packed column to a reactor. In Example 3, the mixture of the fluid and the composition in the reactor were submitted to UV radiation in order to enhance the oxidation rate of the organic compounds that cause the unpleasant and/or undesirable odor. The UV radiation was produced by a 254 nm lamp at a power of 9 Watts. After a predetermined residence time in the reactor, the mixture is recirculated to the top of the packed column to complete the loop.

These operating conditions were reapeated over more than 30 tests. Each test was carried out over a period of time of about 8 to about 12 hours. The same amount of olfactometry measurements were taken. The results were the following:

odor level at the inlet: 386
odor level after $1^{st}$ treatment: 127
effectiveness after $1^{st}$ treatment: 66%
odor level after $2^{nd}$ treatment: 50
effectiveness after $2^{nd}$ treatment: 86%

It can thus be seen that the results presented in examples 1 to 3 clearly show that these three different methods permit to considerably reduce the intensity (or odor level) of the undesirable odor. It can thus be the that such methods permit to efficiently at least partially reduce the intensity or an undesirable or unpleasant odor.

The methods have been described with regard to specific examples. The description as much as the drawings were intended to help the understanding of the document, rather than to limit its scope. It will be apparent to one skilled in the art that various modifications may be made to the methods previously defined without departing from the scope of the document as described herein, and such modifications are intended to be covered by the present document.

What is claimed is:

1. An acidic aqueous oxidizing composition comprising at least one cation of a metal chosen from Fe, Cu, Ni, Mn, Ti, Cr, Ce, Zn, Pd, Mo, and mixtures thereof, $H_2O_2$, and oxalic acid, wherein said acidic aqueous oxidizing composition has a pH of about 1.5 to less than 3.0.

2. The composition of claim 1, wherein said composition comprises a metal cation of Fe.

3. The composition of claim 1, wherein said composition comprises $Fe^{2+}$.

4. The composition of claim 3, wherein said composition comprises $FeSO_4$.

5. The composition of claim 3, wherein said acidic aqueous oxidizing composition has a pH of about 1.5 to about 2.0.

6. The composition of claim 3, wherein said acidic aqueous oxidizing composition has a pH of about 2.0 to less than 3.0.

7. The composition of claim 3, wherein said acidic aqueous oxidizing composition has a pH of about 1.8 to about 2.4.

8. The composition of claim 3, wherein said acidic aqueous oxidizing composition has a pH of about 2.2 to about 2.6.

9. The composition of claim 3, wherein said acidic aqueous oxidizing composition has a pH of about 2.5 to less than 3.0.

10. The composition of claim 3, wherein said acidic aqueous oxidizing composition has a pH of about 2.5 to about 2.8.

11. A method of using the composition of claim 3, wherein said method comprises contacting said composition with a gas having an undesirable odor so as to treat said gas.

12. An acidic aqueous oxidizing composition comprising at least one cation of a metal chosen from Fe, Cu, Ni, Mn, Ti, Cr, Ce, Zn, Pd, Mo, and mixtures thereof, $H_2O_2$, and a sequestering agent chosen from ethylenediaminetetraacetic acid, oxalic acid, citric acid, glycine, NTA, salicylic acid, sulfosalicylic acid, trithylenetetramine, and mixtures thereof, wherein said acidic aqueous oxidizing composition has a pH of about 1.5 less than 3.0.

13. The composition of claim 12, wherein said composition comprises $Fe^{2+}$.

14. The composition of claim 13, wherein said acidic aqueous oxidizing composition has a pH of about 1.5 to about 2.0.

15. The composition of claim 13, wherein said acidic aqueous oxidizing composition has a pH of about 2.0 to less than 3.0.

16. The composition of claim 13, wherein said acidic aqueous oxidizing composition has a pH of about 1.8 to about 2.4.

17. The composition of claim 13, wherein said acidic aqueous oxidizing composition has a pH of about 2.2 to about 2.6.

18. The composition of claim 13, wherein said acidic aqueous oxidizing composition has a pH of about 2.5 to less than 3.0.

19. The composition of claim 13, wherein said acidic aqueous oxidizing composition has a pH of about 2.5 to about 2.8.

* * * * *

UNITED STATES PATENT AND TRADEMARK OFFICE
CERTIFICATE OF CORRECTION

| | | |
|---|---|---|
| PATENT NO. | : 9,522,206 B2 | Page 1 of 1 |
| APPLICATION NO. | : 14/836757 | |
| DATED | : December 20, 2016 | |
| INVENTOR(S) | : Martin Beaulieu et al. | |

It is certified that error appears in the above-identified patent and that said Letters Patent is hereby corrected as shown below:

In the Claims

Claim 12, Column 8, Line 39, change "trithylenetetramine" to --triethylenetetramine--;

Claim 12, Column 8, Line 41, change "1.5 less than 3.0" to --1.5 to less than 3.0--.

Signed and Sealed this
Twenty-first Day of March, 2017

Michelle K. Lee
*Director of the United States Patent and Trademark Office*